United States Patent [19]

Saari et al.

[11] 4,064,138

[45] Dec. 20, 1977

[54] AMINO ACID DERIVATIVES

[75] Inventors: Albert L. Saari, Minneapolis; Ray H. Anderson, Champlin, both of Minn.

[73] Assignee: General Mills, Inc., Minneapolis, Minn.

[21] Appl. No.: 631,285

[22] Filed: Nov. 12, 1975

[51] Int. Cl.² .............. C07D 233/64; C07C 101/24; A61K 7/18
[52] U.S. Cl. .................. 548/344; 260/326.2; 260/534 R; 260/534 L; 424/52
[58] Field of Search ............. 260/534 L, 309, 326.2; 424/52

[56] References Cited

U.S. PATENT DOCUMENTS

| 3,413,326 | 11/1968 | Schmidt | 260/534 L |
|---|---|---|---|
| 3,642,979 | 2/1972 | Irani | 424/52 |
| 3,662,059 | 5/1972 | Wiesner et al. | 424/52 |
| 3,678,154 | 7/1972 | Widder et al. | 424/52 |
| 3,939,262 | 2/1976 | Kim | 424/52 |

Primary Examiner—Joseph E. Evans
Attorney, Agent, or Firm—Gene O. Enockson

[57] ABSTRACT

Disclosed are amino acid derivatives including amino acid fluoride phosphates and alkali metal amino acid fluoride phosphates.

12 Claims, No Drawings

AMINO ACID DERIVATIVES

The present invention relates to a chemical compound or mixture of compounds and more particularly to derivatives of amino acids.

In the past, various derivatives of amino acids have been known, for example, L-lysine succinate has been prepared for addition to foods to provide a nutritional balance of amino acids. Other known derivatives include L-lysine hydrochloride and L-lysine phosphate. The present invention provides a new class of amino acid derivatives having cariostatic properties. The term "fluoride phosphate derivatives" and the like as used herein, unless otherwise specified, shall mean the following amino acid single and double salt derivatives: monofluorophosphate, hydrofluoride phosphate, hydrofluoride monofluorophosphate, dimonofluorophosphate and phosphate monofluorophosphate. The term "amino acid" as used herein will mean the basic amino acids such as lysine, hydroxylysine, arginine, histidine and ornithine. Illustrative of such fluoride phosphate derivatives are the following:

L-lysine monofluorophosphate

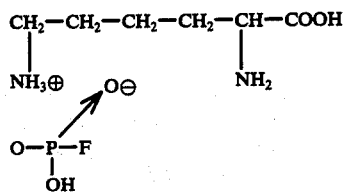

L-lysine hydrofluoride phosphate

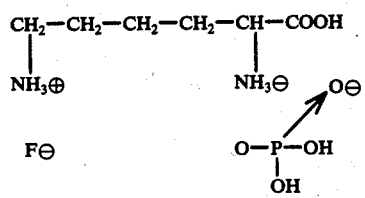

L-lysine hydrofluoride monofluorophosphate

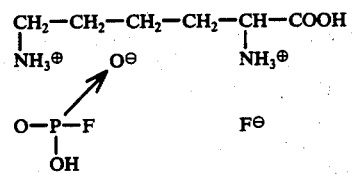

L-lysine di-monofluorophosphate

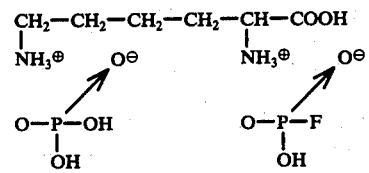

L-lysine phosphate monofluorophosphate

In practice the derivative may be an isomer mixture, for example, a mixture as follows:

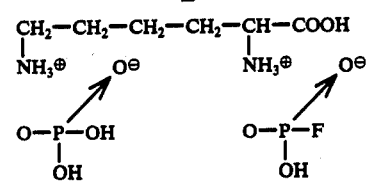

and

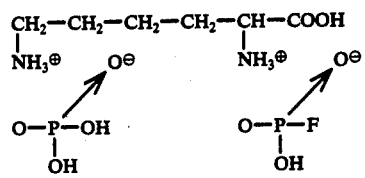

Similar derivatives suitable as cariostatic agents may be prepared from hydroxylysine, arginine, histidine, and ornithine. Although the L-forms of the amino acids are preferred, the D and DL-forms may be used. Illustrative of such derivatives are the following:

Hydroxylysine monofluorophosphate

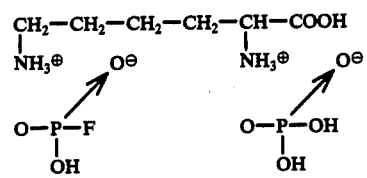

Arginine hydrofluoride phosphate

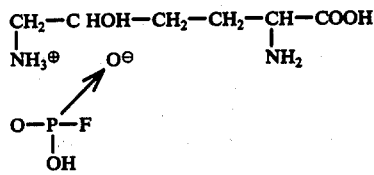

Histidine hydrofluoride monofluorophosphate

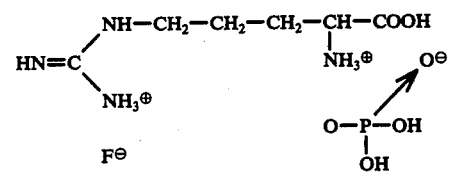

Ornithine di-monofluorophosphate

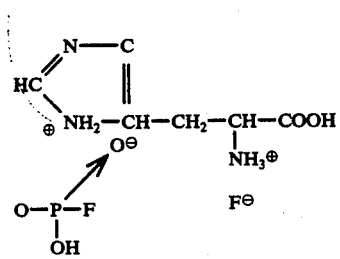

$$\begin{array}{c} \text{CH}_2-\text{CH}_2-\text{CH}_2-\text{CH}-\text{COOH} \\ | \qquad\qquad\qquad | \\ \text{NH}_3^{\oplus} \quad \text{O}^{\ominus} \quad\;\; \text{NH}_3^{\oplus} \quad \text{O}^{\ominus} \\ \nwarrow \qquad\qquad\qquad \nwarrow \\ \text{O}-\text{P}-\text{F} \qquad\; \text{O}-\text{P}-\text{F} \\ | \qquad\qquad\qquad | \\ \text{OH} \qquad\qquad\; \text{OH} \end{array}$$

One general formula for the amino acid derivative of the present invention may be expressed as follows:

$$\begin{array}{c} \text{R}-\text{CH}_2-\text{CH}-\text{COOH} \\ \oplus \qquad\qquad | \\ \text{A}^{\ominus} \qquad\quad \text{NH}_3^{\oplus} \\ \text{B}^{\ominus} \end{array}$$

where R+ is one of the following:

$$-(\text{C X H})_n-\text{NH}_3^{\oplus}$$

$$\begin{array}{c} -(\text{CH}_2)_2-\text{NH}-\text{C}=\text{NH} \\ | \\ \text{NH}_3^{\oplus} \end{array}$$

$$\begin{array}{c} -\text{C}=\!=\!=\text{CH} \\ | \qquad\quad \| \\ \oplus\text{NH}_2 \quad\; \text{N} \\ \diagdown \;\; \diagup \\ \text{C} \\ \text{H} \end{array}$$

$$\begin{array}{c} \ominus \\ \boxed{\phantom{xx}} \\ \text{N} \\ \text{H}_2^{\oplus} \end{array}$$

X is hydrogen or a hydroxyl group.
$n$ is an integer preferably 2 or 3.
$A^-$ is $F^-$, $H_2PO_4^-$ or $HPO_3F^-$.
$B^-$ is $F^-$, $H_2PO_4^-$ or $HPO_3F^-$.
Wherein $A^-$ is $F^-$ or $HPO_3F^-$ when $B^-$ is $H_2PO_4^-$ and $A^-$ is $HPO_3F^-$ or $H_2PO_4^-$ when $B^-$ is $F^-$. And $B^-$ is $F^-$ or $HPO_3F^-$ when $A^-$ is $H_2PO_4^-$ and $B^-$ is $HPO_3F^-$ or $H_2PO_4^-$ when $A^-$ is $F^-$.

A second general formula for the amino acid derivative of the present invention may be expressed as follows:

$$\begin{array}{c} \text{R}-\text{CH}_2-\text{CH}-\text{COOH} \\ | \\ \text{NH}_3^{\oplus} \\ \\ \text{D}^{\ominus} \end{array}$$

Where R is one of the following:

$$-(\text{C X H})_n-\text{NH}_2$$

$$\begin{array}{c} -(\text{CH}_2)_2-\text{NH}-\text{C}=\text{NH} \\ | \\ \text{NH}_2 \end{array}$$

$$\begin{array}{c} -\text{C}=\!=\!=\text{CH} \\ | \qquad\quad \| \\ \text{NH} \quad\;\; \text{N} \\ \diagdown \;\; \diagup \\ \text{O} \end{array}$$

$$\begin{array}{c} \ominus \\ \boxed{\phantom{xx}} \\ \text{N} \\ \text{H} \end{array}$$

X is H or OH.
$n$ is an integer preferably 2 or 3.
$D^-$ is $HPO_3F^-$

A further general formula for the amino acid derivative of the present invention may be expressed as follows:

$$\begin{array}{c} \text{R}-\text{CH}_2-\text{CH}-\text{COOH} \\ \oplus \qquad\qquad | \\ \text{E}^{\ominus} \qquad\quad \text{NH}_2 \end{array}$$

Where R is one of the following:

$$-(\text{C X H})_n-\text{NH}_3^{\oplus}$$

$$\begin{array}{c} -(\text{CH}_2)_2-\text{NH}-\text{C}=\text{NH} \\ | \\ \text{NH}_3^{\ominus} \end{array}$$

$$\begin{array}{c} -\text{C}=\!=\!=\text{CH} \\ | \qquad\quad \| \\ \oplus\text{NH}_2 \quad\; \text{N} \\ \diagdown \;\; \diagup \\ \text{C} \\ \text{H} \end{array}$$

$$\begin{array}{c} \ominus \\ \boxed{\phantom{xx}} \\ \text{NH}_2 \\ \oplus \end{array}$$

X is H or OH
$n$ is an integer preferably 2 or 3
$E^-$ is $HPO_3F^-$

The present invention also includes the alkali metal salts of these compounds. The alkali metals such as sodium or potassium may replace an ionizable hydrogen in the phosphate or carboxylic group.

The amino acid fluoride phosphate of the present invention, may be prepared by any of several routes. It is important to combine the components in suitable stoichiometric amounts in a suitable mutual solvent such as water, glycerol or dilute alcohol. For example, an aqueous solution of the freebase of the amino acid may be mixed with a stoichiometric amount of a hydrogen fluoride aqueous solution and then mixed with a stoichiometric amount of ortho-phosphoric acid. The water is preferably removed from the resulting solution to produce an anhydrous amino acid hydrogen fluoride phosphate. The water may be removed by vacuum distillation. However, the preparations may be utilized as their aqueous solutions.

Alternatively, the solution may be first concentrated by vacuum distillation or evaporation, for example, to a concentration of about 25–35 percent amino acid hydrogen fluoride phosphate and then precipitated, for example, by the addition of a water miscible, non-reactive organic solvent in which the amino acid derivative is insoluble such as a concentrated monohydroxyl alcohol, typically, ethanol, methanol, propanol or such as alcohol together with an ether such as ethyl ether, or a mixture of such alcohol with an ester. The preferred solvent is a mixture of ethanol and methanol. The precipitated amino acid hydrogen fluoride phosphate may then be air dried and if desirable, ground to a free flowing form.

throughout the processing, it is desirable to reduce any degradation such as by excluding air and by controlling the reaction temperatures. For example, if the hydrogen fluoride is added in the presence of air, it is desirable to maintain the temperature below about 75°

C. or added at higher temperature over a short period of time such as less than 15 minutes.

The amino acid alkali metal fluoride phosphate may be prepared by reacting the free-base amino acid first with the alkali metal di-hydrogen phosphate and then reacting the product with hydrogen fluoride or hydrofluoric acid. The water then may be removed, for example, by vacuum distillation or as previously described with water miscible organic solvent.

The amino acid fluorophosphate may be prepared by reacting the free-base amino acid with a stoichiometric amount of monofluorophosphoric acid. The water may be then removed as previously described. If one desires to prepare the alkali metal salt of the amino acid monofluorphosphate, this may be accomplished by adding a stoichiometric amount of the hydroxide of the particular alkali metal, for example, by the addition of sodium hydroxide or potassium hydroxide to the amino acid fluorophosphate while in the aqueous solution. The water may then be removed from the salt.

Another approach for preparing the alkali metal salt of the amino acid monofluorophosphate is by reacting the free base lysine with 1/2 stoichiometric amount of monofluorophosphoric acid and then reacting the product with a 1/2 stoichiometric amount of the alkali metal monofluorophosphate, for example, di-sodium monofluorophosphate. The water may then be removed from the resulting monosodium salt of the amino acid monofluorophosphate.

A further approach for preparing the composition of the present invention is to prepare a glycerol solution of the free base amino acid starting with the free-base amino acid in a solid or granular form. Free-base amino acid is generally prepared by converting the halogen salt of the amino acid to the free amino acid usually by an ion exchange column. One may, for example, prepare a solution of free-base amino acid in glycerol and add a stoichiometric amount of hydrogen fluoride or hydrofluoric acid and then react the product with a one stoichiometric amount of orthophosphoric acid. If one is preparing an additive for a dentifrice or mouthrinse, this may be a preferred approach since one need only adjust the concentration of the active compound by the addition of glycerol to achieve the desired concentration. Alternatively, the glycerol solution may be saturated with regard to the amino acid.

It is generally accepted that dental carries require a cariogenic microflora, a fermentable substrate and a vulnerable host system. The amino acid fluoride phosphate of the present invention has been found useful in reducing the cariogenic microflora. The amino acid fluoride phosphate may be applied by any of a variety of techniques. For example, it may be applied by a dentist as a topical application. It may be included in a mouth wash, toothpaste, chewing gum and the like. The amino acid fluoride phosphate may be used as an aqueous solution or suspension. Alternatively, the amino acid fluoride phosphate may be in the form of a solution in an organic solvent such as in glycerol.

Since glycerol tends to increase the cariostatic activity of the present amino acid derivative and is a good solvent for such compounds, it is preferred that the compound be prepared and used as the glycerol solution. A stock solution having a concentration of amino acid derivative sufficient to provide perhaps 10,000 to 20,000 ppm fluoride in glycerol may be prepared. The stock solution may be readily diluted with glycerol to an appropriate concentration of the amino acid derivative for incorporation into the end product.

A glycerol solution, for example, of the acid form of lysine hydrogenfluoride phosphate containing about 10,000 ppm fluoride may be painted on the tooth surface by a dentist and then rinsed off after 2 to 5 minutes. This is similar to the conventional methods for topical fluoride treatments employed by most dentists except for use of the present amino acid derivative. Alternatively, a gel may be prepared including the glycerol solution. The gel is then placed in a mouth piece and held in the mouth for the desired treatment time.

Modern dentifrices typically contain glycerol as a solvent. Thus the amino acid derivative of the present invention may be used by inclusion in the glycerol portion of conventional dentifrices. The derivative may be used at a level to provide 10,000 ppm fluoride based on the weight of the glycerol.

The amino acid derivative may be incorporated into any conventional glycerol or water based mouthwash to give a concentration of between about 50 to 100 ppm fluoride in the mouthwash.

The solid alkali metal salts of the present amino acid derivatives, especially the sodium and potassium salts may be used as food additives. A desirable intake level is about 1 mg of fluoride per day. For example, the salt may be included in sucrose at a level of about 8 ppm fluoride.

The present amino acid derivative may be incorporated into the formulation of conventional chewing gum at a level of about 0.1 to 0.2 mg of fluoride per stick of gum. The gum may also include glycerol.

In addition to cariostatic uses, these compounds may be used as dietary and/or therapeutic supplements for persons having fluoride deficiencies such as osteoporosis.

The following examples are for purposes of illustrating the present invention.

EXAMPLE I

An amino acid fluoride phosphate according to the present invention was prepared by passing 18.6 grams of L-lysine-HCL and 50 milliliters of water through a column containing 100 ml. of Amberlight IRA 410™ in the OH−-form. Four grams of hydrofluoric acid (a 50% aqueous solution of hydrogen fluoride) were added to the resulting free lysine solution. The solution was then concentrated to about 70 ml. using a vacuum evaporator. 13.6 grams of mono-potassium phosphate and 20 ml. of water were added. The mixture was stirred and warmed slightly to dissolve all the components. The resulting solution was poured into 800 ml. of methanol producing a cloudy suspension. After 2 hours, the precipitate was collected in a filter. The precipitate was then resuspended in 200 ml. of methanol and again filtered. The cake was then air-dried. The product was the mono-potassium salt of lysine hydrofluoride phosphate. Rat tests were conducted to determine cariostatic properties of the lysine hydrofluoride phosphate. Three groups of rats were used. The control group was fed a standard rat high sucrose cariogenic diet for 30 days. The second group was fed the same diet but with the lysine hydrofluoride phosphate added in an amount sufficient to provide 9 parts per million (ppm) fluoride. The third group was fed the same diet but with the amino acid replaced with sodium fluoride (9 ppm fluoride). Each group was sacrificed. The jaws were removed and autoclaved to remove the flesh. Carious lesions were visualized with dye and counted under a microscope. The second group had a 24% lower incidence of caries as compared to the other groups.

EXAMPLE II

Lysine hydrofluoride phosphate was prepared according to the present invention passing an aqueous solutions containing 120 grams of L-lysine-HCL through a 400 ml. column of Amberlight IRA 410 resin in the OH$^-$ form. The eluate was treated with 24 grams of a 50% aqueous solution of hydrogen flouride while being cooled with ice. Then 60 grams of orthophosphoric acid were added. The resulting solution was evaporated to produce a heavy, slightly cloudy syrup in a rotary evaporator in vacuo. The concentrated solution was treated with a small amount of methanol to produce a cloudy syrup. The cloudy syrup was an aqueous solution of lysine hydroflouride phosphate. The syrup was added to a rat diet as described in Example I and resulted in a caries reduction of 23%.

EXAMPLE III

Amino acid fluorophosphate was prepared by adding 1 mole of fluorophosphoric acid to 0.5 moles of free base lysine. The solution was evaporated to a heavy syrup using a vacuum evaporator. The remaining water was removed by azeotropic distillation using absolute ethanol and benzene. The resulting very thick syrup was dried over calcium chloride in a vacuum desiccator. The product was found to be L-lysine di-monofluorophosphate.

EXAMPLE IV

The sodium salt of L-lysine monofluorophosphate was prepared by combining 0.2 moles of free base lysine, 0.1 mole fluorophosphoric acid and 0.1 mole disodium monofluorophosphate. Water was removed by a vacuum evaporator and the resulting concentrated syrup was poured into about 600 ml. of an equal mixture of ethanol and methanol. A grainy salt precipitated. After filtration, the filter cake was washed with methanol and then air dried. The product was the sodium salt of monofluorophosphate.

EXAMPLE V

The potassium salt of L-lysine hydrofluoride phosphate was prepared by adding 0.1 mole hydrofluoric acid to 0.1 mole free base lysine. The resulting solution was concentrated by vacuum distillation and 1 mole of potassium phosphate ($KH_2PO_4$) was added with about 20 ml. of water. The mixture was slightly warmed and a clear solution resulted. The solution was poured into about 800 ml. of methanol with vigorous stirring. A salt suspension resulted. The salt was separated by filtration and washed with methanol. The washed salt was air dried. The product was the potassium salt of L-lysine hydrofluoride phosphate.

EXAMPLE VI

L-ornithine hydrofluoride phosphate was prepared by adding 0.1 mole hydrofluoric acid to 0.1 mole free base ornithine and then adding 0.1 mole of orthophosphoric acid. The resulting solution was concentrated in a vacuum evaporator and poured into 350 ml. of a methanol-ethanol mixture. A gummy precipitate resulted. The precipitate was then dried over calcium chloride in a desiccator. The product was L-ornithine hydrofluoride phosphate.

EXAMPLE VII

L-ornithine monofluorophosphate was prepared by adding 0.1 mole of monofluorophosphoric acid to 0.1 mole of free base ornithine. The resulting solution was concentrated using a vacuum evaporator. The concentrated solution was added to a 50:50 mixture of methanol and absolute ethyl alcohol. A gummy precipitate resulted. The precipitate was L-ornithine monofluorophosphate.

EXAMPLE VIII

L-lysine monofluorophosphate was prepared by combining 29.2 grams of free-base lysine with 20 gm. (grams) of monofluorophosphoric acid in about 75 ml. of water. The resulting clear syrupy solution was poured into 750 ml. of a 50:50 mixture of methanol and ethanol (absolute) to precipitate the solid salt. The cake was collected after filtration and rinsed with methanol. The product (L-lysine monofluorophosphate) was then air dried. The L-lysine monofluorophosphate was tested in rat diets as described in Example I but at a level of 6.8 ppm fluoride. Caries reduction was 36%.

A second test was conducted in which extracted sound human teeth were etched with 0.025 N lactic acid for 30 minutes to present a clean tooth surface and then dried. The teeth were next etched for 5 minutes in fresh 0.025 N lactic acid. The calcium concentration of this lactic acid solution was determined to provide a base point. The teeth were then treated with a 16 ppm fluoride, by weight, aqueous solution of the L-lysine monofluorophosphate for 2 minutes. The treated teeth were then etched again for 5 minutes in fresh 0.025 N lactic acid. The calcium concentration of this solution was found to be 8% less than that of the earlier solution, thus showing that the present lysine derivative reduced enamel dissolution by 8%.

A glycerol solution of the lysine derivative (1.2% by weight) was applied to rats on the 12th day of life. The derivative was applied by inserting two drops in the rats' mouth at a 3 hour interval. These rats were placed on the aforementioned cariogenic diet and fed for 28 days. The rats were sacrificed and the caries determined as previously described. This topical application provided a 24% reduction in caries as compared to a control group.

EXAMPLE IX

L-arginine monofluorophosphate was prepared by combining 34.8 gm. of free-base L-arginine with 20 gm. of monofluorophosphoric acid in about 75 ml. of water. The resulting clear syrup was poured into 750 ml. of a mixture of methanol and ethanol. This was allowed to stand over night and the salt was collected by filtration. The resulting L-arginine monofluorophosphate was then rinsed with methanol and air dried.

EXAMPLE X

L-histidine monofluorophosphate was prepared by combining 31 gm. of free-base L-histidine with 20 gm. of monofluorophosphoric acid in about 75 ml. of water. A clear syrup resulted. The syrup was poured into 750 ml. of a methanol-ethanol mixture. The precipitate (L-histidine monofluorophosphate) was collected and vacuum dried in a desiccator.

EXAMPLE XI

L-arginine hydrofluoride phosphate was prepared by combining 34.8 gm. of L-arginine (free-base) with 8 gm.

of a 50% aqueous solution of hydrofluoride and 23.5 gm. of orthophosphoric acid. This was dissolved in about 75 ml. of water. The resulting syrup was poured into about 750 ml. of a methanol-ethanol mixture to precipitate the salt. After filtration the cake (L-arginine hydrofluoride phosphate) was rinsed with methanol and air dried.

Enamel dissolution tests were conducted as described in Example VIII; however, using L-arginine hydrofluoride phosphate at a level of 2.4 ppm fluoride. Enamel dissolution reduction was 7%.

EXAMPLE XII

Free-base L-lysine was prepared from L-lysine-HCL by passing same through an Amberlight IRA 410 TM resin in the OH⁻ form. The eluate of free base lysine was then concentrated to a heavy syrup in a rotary vacuum evaporator. A mixture of ethanol and benzene was then added to the heavy syrup to remove the residual water by azeotropic distillation. The free base lysine was then dried in air. 29.2 gm. of the free-base L-lysine were slowly dissolved in 32 gm. of glycerol and then 19.8 gm. of monofluorophosphoric acid were added. Some frothing occurred and then subsided. The resulting solution of L-lysine monofluorophosphate was diluted with 400 gm. of glycerol.

L-lysine monofluorophosphate was subjected to the enamel dissolution test described in Example VIII. The L-lysine monofluorophosphate aqueous solution contained 7.7 ppm fluoride. The enamel dissolution reduction was 13%.

EXAMPLE XIII

A glycerol solution of L-lysine hydrofluoride phosphate was prepared by dissolving 29.2 gm. of the free L-lysine described in Example XII in 340 gm. of glycerol. Then 8 gm. of a 50% aqueous solution of hydrogen fluoride were added. Next, 23 gm. of orthophosphoric acid were added and marked frothing occurred. Upon subsiding, the solution was made up to 400 gm. with glycerol.

A soy trypticiase standard media was inoculated with a known member of *Streptococcus mutans* microorganisms. Such microorganisms are known to produce dental caries. The glycerol solution of L-lysine hydrofluoride phosphate was added at a level of 45 ppm fluoride based on the weight of the media. The media was then incubated for 16 hours and a plate count was taken to determine the growth of the organisms.

An identical media was prepared and inoculated. Sodium fluoride was added in an amount sufficient to provide 50 ppm fluoride in the media. This media was incubated for 16 hours and a plate count was taken to determine the growth of organisms.

A control media was identically prepared and inoculated. The media was incubated for 16 hours. A plate count was then taken to determine the organism growth.

The organism growth in the amino acid derivative containing media was only 24% of that of the control. The organism growth of the sodium fluoride containing media was 57% of that of the control.

EXAMPLE XIV

A glycerol solution of L-arginine monofluorophosphate was prepared by dissolving 17.4 gm. free base L-arginine in 173 gm. of glycerol. Then 9.9 gm. of monofluorophosphoric acid were added. The resulting solution was permitted to cool and the solution was made up to 200 gm. with glycerol.

EXAMPLE XV

A glycerol solution of L-arginine hydrofluoride phosphate was prepared by suspending 17.4 gm. of free base L-arginine in 167 gm. of glycerol. To this solution, 4 gm. of a 50% aqueous solution of hydrofluoric acid were added. Then 11.5 gm. of orthophosphoric acid were added. Following cooling, the solution was diluted to 200 gm. with glycerol.

The inhibiting effect on microorganism growth was determined as described in Example XIII. The present amino acid derivative at 60 ppm fluoride was found to limit the microorganism growth to only 17% of that of the control.

The effect on enamel dissolution was determined as described in Example VIII. The amino acid derivative at a level of 6 ppm fluoride resulted in a 24% reduction in enamel dissolution.

EXAMPLE XVI

A glycerol solution of L-histidine hydrofluoride phosphate was prepared by suspending 15.5 gm. of free-base L-histidine in 168 gm. of glycerol. Then 4 gm. of a 50% aqueous solution of hydrofluoric acid and 11.5 gm. of orthophosphoric acid were added. The mixture slowly dissolved over night to yield a slightly cloudy solution. The resulting solution was diluted to about 200 gm. with glycerol.

The L-histidine hydrofluoride at a level 5.5 ppm fluoride provided an 18% reduction in enamel dissolution. This amino acid derivative at a level of 60 ppm fluoride resulted in a microbial growth of 53% of that of a control.

EXAMPLE XVII

A glycerol solution of L-lysine hydrofluoride phosphate was prepared by dissolving 28.5 gm. of L-lysine hydrofluoride in about 400 gm. of glycerol. Then 28.5 gm. of orthophosphoric acid were added and a clear solution resulted. The solution was then diluted to a total of about 500 gm. with glycerol.

The embodiments of the invention in which an exclusive property or privilege is claimed are defined as follows:

1. An amino acid derivative selected from the group consisting of amino acid monofluorophosphate, amino acid hydrofluoride phosphate, amino acid hydrofluoride monofluorophosphate, amino acid di-monofluorophosphate, amino acid phosphate monofluorophosphate and their alkali metal salts, said amino acids being selected from the group consisting of lysine, hydroxylysine, arginine, histidine and ornithine.

2. The amino acid derivative of claim 1 wherein said alkali metal salts are selected from the group consisting of the sodium and potassium salts.

3. A glycerol solution of the amino acid derivative of claim 1.

4. An amino acid derivative comprising basic amino acid fluoride phosphate, said amino acid comprising lysine, hydroxylysine, arginine, histidine or ornithine.

5. The amino acid derivative of claim 4 wherein said basic amino acid fluoride phosphate is a member selected from the group consisting of lysine monofluorophosphate, lysine hydrofluoride phosphate, lysine hydrofluoride monofluorophosphate, lysine di-monofluorophosphate, lysine hydrofluoride monofluorophosphate, lysine di-monofluorophosphate and lysine phosphate monofluorophosphate.

6. The amino acid derivative of claim 4 wherein said basic amino acid fluoride phosphate is a member selected from the group consisting of hydroxylysine monofluorophosphate, hydroxylysine hydrofluoride phosphate, hydroxylysine hydrofluoride monofluorophosphate, hydroxylysine di-monofluorophosphate, hydroxylysine hydrofluoride monofluorophosphate, hydroxylysine di-monofluorophosphate and hydroxylysine phosphate monofluorophosphate.

7. The amino acid derivative of claim 4 wherein said basic amino acid fluoride phosphate is a member selected from the group consisting of arginine monofluorophosphate, arginine hydrofluoride phosphate, arginine hydrofluoride monofluorophosphate, arginine di-monofluorophosphate, arginine hydrofluoride monofluorophosphate, arginine di-monofluorophosphate and arginine phosphate monofluorophosphate.

8. The amino acid derivative of claim 4 wherein said basic amino acid fluoride phosphate is a member selected from the group consisting of histidine monofluorophosphate, histidine hydrofluoride phosphate, histidine hydrofluoride monofluorophosphate, histidine di-monofluorophosphate, histidine hydrofluoride monofluorophosphate, histidine di-monofluorophosphate and histidine phosphate monofluorophosphate.

9. The amino acid derivative of claim 4 wherein said basic amino acid fluoride phosphate is a member selected from the group consisting of ornithine monofluorophosphate, ornithine hydrofluoride phosphate, ornithine hydrofluoride monofluorophosphate, ornithine di-monofluorophosphate, ornithine hydrofluoride monofluorophosphate, ornithine di-monofluorophosphate and ornithine phosphate monofluorophosphate.

10. An amino acid derivative having the general formula:

$$R-CH_2-CH-COOH$$
$$\overset{\oplus}{A^{\ominus}} \quad \overset{|}{NH_3^{\oplus}}$$
$$B^{\ominus}$$

Wherein R+ is a member of the group consisting of

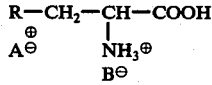

$$-(CH_2)_2-NH-\underset{\underset{NH_3^{\oplus}}{|}}{C}$$

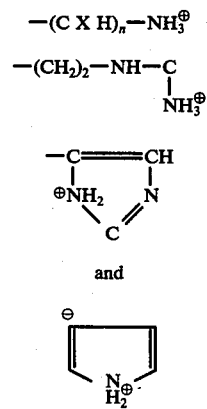

and

X is H or OH
n is an integer of 2 or 3
A− is F−, H₂PO₄− or HPO₃F−
B− is F−, H₂PO₄− or HPO₃F−
Wherein A− is F− or HPO₃F− when B− is H₂PO₄− and A− is HPO₃F− or H₂PO₄− when B− is F−
And B− is F− or HPO₃F− when A− is H₂PO₄− and B− is HPO₃F− or H₂PO₄− when A− is F−.

11. An amino acid derivative having the general formula:

$$R-CH_2-CH-COOH$$
$$\overset{|}{NH_3^{\oplus}}$$
$$D^{\ominus}$$

Wherein R is a member of the group consisting of:

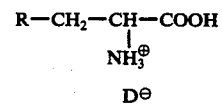

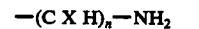
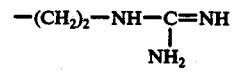

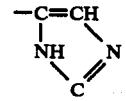

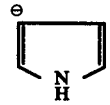

X is H or OH
n is an integer of 2 or 3
D− is HPO₃F−.

12. An amino acid derivative having the general formula:

$$R-CH_2-CH-COOH$$
$$\overset{\oplus}{E^{\ominus}} \quad \overset{|}{NH_2}$$

Wherein R+ is a member of the group consisting of:

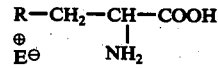

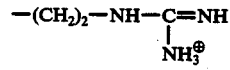

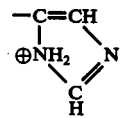

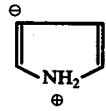

X is H or OH
n is an integer of 2 or 3
E− is HPO₃F−.

* * * * *

UNITED STATES PATENT AND TRADEMARK OFFICE
CERTIFICATE OF CORRECTION

PATENT NO. : 4,064,138
DATED : December 20, 1977
INVENTOR(S) : Albert L. Saari & Ray H. Anderson It is certified that error appears in the above-identified patent and that said Letters Patent are hereby corrected as shown below:

In column 1, under L-lysine dimonofluorophosphate, the formula that reads:

" 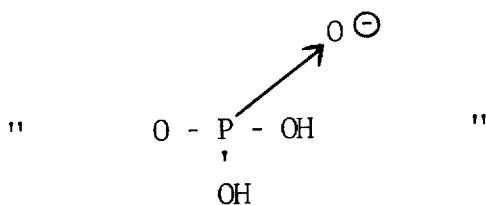 "

should read:

-- 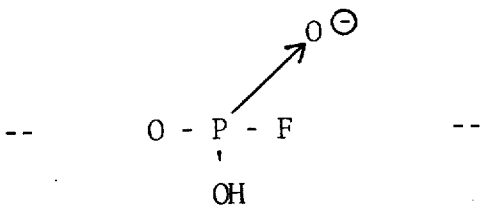 --

In column 3, line 17: delete " R+ " and insert -- R⊕ --

UNITED STATES PATENT AND TRADEMARK OFFICE
CERTIFICATE OF CORRECTION

PATENT NO. : 4,064,138
DATED : December 20, 1977
INVENTOR(S) : Albert L. Saari & Ray H. Anderson It is certified that error appears in the above-identified patent and that said Letters Patent are hereby corrected as shown below:

In column 3, lines 25-29 approximately, the formula that reads:

" 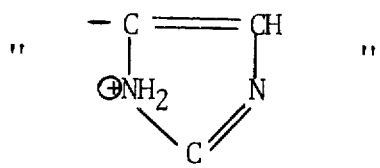 "

should read:

-- 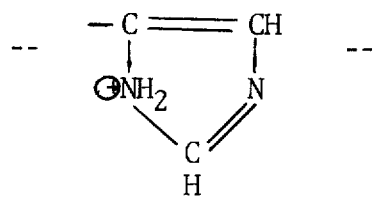 --

UNITED STATES PATENT AND TRADEMARK OFFICE
CERTIFICATE OF CORRECTION

PATENT NO. : 4,064,138
DATED : December 20, 1977
INVENTOR(S) : Albert L. Saari & Ray H. Anderson It is certified that error appears in the above-identified patent and that said Letters Patent are hereby corrected as shown below:

In column 3, lines 29-34 approximately, the formula that reads:

" 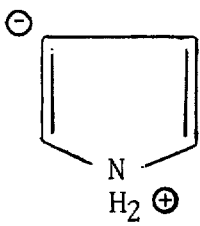 "

should read:

-- 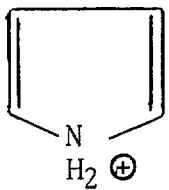 --

UNITED STATES PATENT AND TRADEMARK OFFICE
CERTIFICATE OF CORRECTION

PATENT NO. : 4,064,138

DATED : December 20, 1977

INVENTOR(S) : Albert L. Saari & Ray H. Anderson

It is certified that error appears in the above-identified patent and that said Letters Patent are hereby corrected as shown below:

In column 3, lines 37-42 delete:

" $A^-$ is $F^-$, $H_2PO_4^-$ or $HPO_3F^-$.
$B^-$ is $F^-$, $H_2PO_4^-$ or $HPO_3F^-$.
Wherein $A^-$ is $F^-$ or $HPO_3F^-$ when $B^-$ is $H_2PO_4^-$ and $A^-$ is $HPO_3F^-$ or $H_2PO_4^-$ when $B^-$ is $F^-$. And $B^-$ is $F^-$ or $HPO_3F^-$ when $A^-$ is $H_2PO_4^-$ and $B^-$ is $HPO_3F^-$ or $H_2PO_4^-$ when $A^-$ is $F^-$. "

and insert:

-- $A^\ominus$ is $F^\ominus$, $H_2PO_4^\ominus$ or $HPO_3F^\ominus$.
$B^\ominus$ is $F^\ominus$, $H_2PO_4^\ominus$ or $HPO_3F^\ominus$.
Wherein $A^\ominus$ is $F^\ominus$ or $HPO_3F^\ominus$ when $B^\ominus$ is $H_2PO_4^\ominus$ and $A^\ominus$ is $HPO_3F^\ominus$ or $H_2PO_4^\ominus$ when $B^\ominus$ is $F^\ominus$. And $B^\ominus$ is $F^\ominus$ or $HPO_3F^\ominus$ when $A^\ominus$ is $H_2PO_4^\ominus$ and $B^\ominus$ is $HPO_3F^\ominus$ or $H_2PO_4^\ominus$ when $A^\ominus$ is $F^\ominus$. --

UNITED STATES PATENT AND TRADEMARK OFFICE
CERTIFICATE OF CORRECTION

PATENT NO. : 4,064,138
DATED : December 20, 1977
INVENTOR(S) : Albert L. Saari & Ray H. Anderson It is certified that error appears in the above-identified patent and that said Letters Patent are hereby corrected as shown below:

In column 3, lines 59-63 approximately, the formula that reads:

" 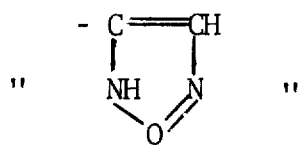 "

should read:

-- 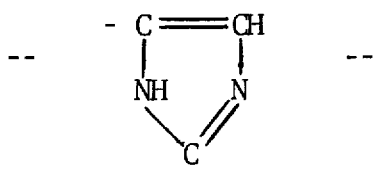 --

UNITED STATES PATENT AND TRADEMARK OFFICE
CERTIFICATE OF CORRECTION

PATENT NO. : 4,064,138

DATED : December 20, 1977

INVENTOR(S) : Albert L. Saari & Ray H. Anderson

It is certified that error appears in the above-identified patent and that said Letters Patent are hereby corrected as shown below:

In column 3, lines 64-67 approximately, the formula that reads:

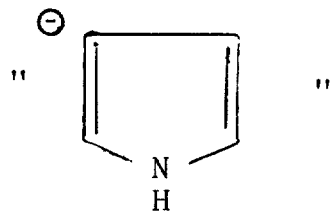

should read:

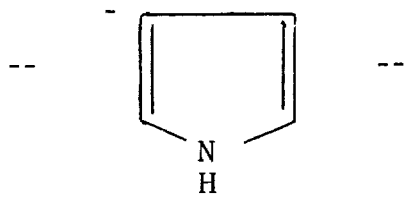

UNITED STATES PATENT AND TRADEMARK OFFICE
CERTIFICATE OF CORRECTION

PATENT NO. : 4,064,138      Page 7 of 14
DATED : December 20, 1977
INVENTOR(S) : Albert L. Saari & Ray H. Anderson It is certified that error appears in the above-identified patent and that said Letters Patent are hereby corrected as shown below:

In column 4, line 3, delete: " $D - $ is $HPO_3F - $ "

and insert: -- $D^{\ominus}$ is $HPO_3F^{\ominus}$ --

In column 4, lines 16-18 approximately, the formula that reads:

"  "

should read:

-- 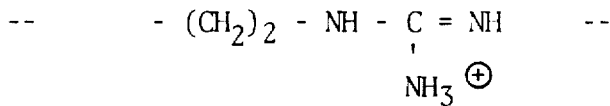 --

UNITED STATES PATENT AND TRADEMARK OFFICE
CERTIFICATE OF CORRECTION

PATENT NO. : 4,064,138
DATED : December 20, 1977
INVENTOR(S) : Albert L. Saari & Ray H. Anderson It is certified that error appears in the above-identified patent and that said Letters Patent are hereby corrected as shown below:

In column 4, lines 24-28 approximately, the formula that reads:

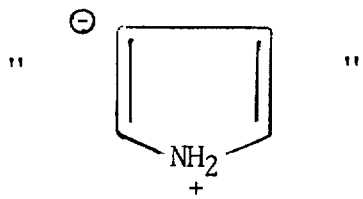

should read

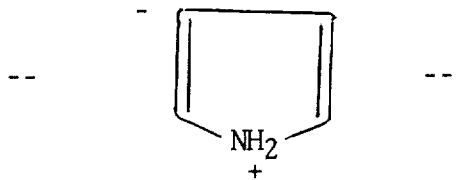

UNITED STATES PATENT AND TRADEMARK OFFICE
CERTIFICATE OF CORRECTION

PATENT NO. : 4,064,138
DATED : December 20, 1977
INVENTOR(S) : Albert L. Saari & Ray H. Anderson It is certified that error appears in the above-identified patent and that said Letters Patent are hereby corrected as shown below:

In column 4, line 31, delete: " E - is $HPO_3F$ - "

and insert: -- $E^{\ominus}$ is $HPO_3F^{\ominus}$ --

In column 4, line 57, delete " as " and insert -- an --.

In column 4, line 64, delete "throughout" and insert -- Throughout --.

In column 6, line 45, delete "OH - " and insert -- $OH^-$ --.

In column 7, line 7, after " invention " and insert -- by --.

In column 7, line 9, after " 410 " and insert -- ™ --.

In column 9, line 15, delete "TM" and insert -- ™ --.

In column 11, line 47, delete " + " and insert -- $\oplus$ --.

UNITED STATES PATENT AND TRADEMARK OFFICE
CERTIFICATE OF CORRECTION

PATENT NO. : 4,064,138
DATED : December 20, 1977
INVENTOR(S) : Albert L. Saari & Ray H. Anderson It is certified that error appears in the above-identified patent and that said Letters Patent are hereby corrected as shown below:

In column 11, lines 61 - 64 approximately, the formula that reads:

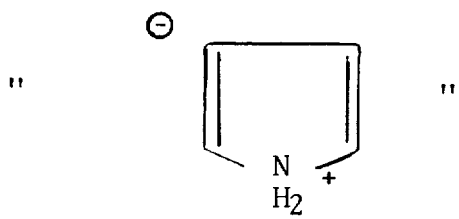

should read:

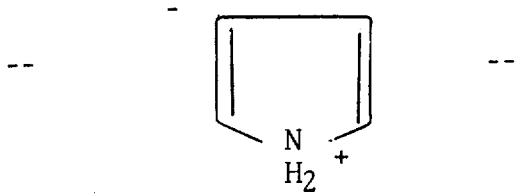

UNITED STATES PATENT AND TRADEMARK OFFICE
CERTIFICATE OF CORRECTION

PATENT NO. : 4,064,138

DATED : December 20, 1977

INVENTOR(S) : Albert L. Saari & Ray H. Anderson

It is certified that error appears in the above-identified patent and that said Letters Patent are hereby corrected as shown below:

In column 12, lines 3-8 delete:

"    A - is F -, $H_2PO_4$ - or $HPO_3F$ -
   B - is F -, $H_2PO_4$ - or $HPO_3F$ -
   Wherein A - is F - or $HPO_3F$ - when B - is $H_2PO_4$ -
     and A - is $HPO_3F$ - or $H_2PO_4$ - when B - is F -
   And B - is F - or $HPO_3F$ - when A - is $H_2PO_4$ - and
     B - is $HPO_3F$ - or $H_2PO_4$ - when A - is F -.      "

and insert:

--  $A^\ominus$ is $F^\ominus$, $H_2PO_4^\ominus$ or $HPO_3F^\ominus$
   $B^\ominus$ is $F^\ominus$, $H_2PO_4^\ominus$ or $HPO_3F^\ominus$
   Wherein $A^\ominus$ is $F^\ominus$ or $HPO_3F^\ominus$ when $B^\ominus$ is $H_2PO_4^\ominus$
     and $A^\ominus$ is $HPO_3F^\ominus$ or $H_2PO_4^\ominus$ when $B^\ominus$ is $F^\ominus$.
   And $B^\ominus$ is $F^\ominus$ or $HPO_3F^\ominus$ when $A^\ominus$ is $H_2PO_4^\ominus$ and
     $B^\ominus$ is $HPO_3F^\ominus$ or $H_2PO_4^\ominus$ when $A^\ominus$ is $F^\ominus$.   --

UNITED STATES PATENT AND TRADEMARK OFFICE
CERTIFICATE OF CORRECTION

PATENT NO. : 4,064,138

DATED : December 20, 1977

INVENTOR(S) : Albert L. Saari & Ray H. Anderson

It is certified that error appears in the above-identified patent and that said Letters Patent are hereby corrected as shown below:

In column 12, lines 28-32 approximately, the formula that reads:

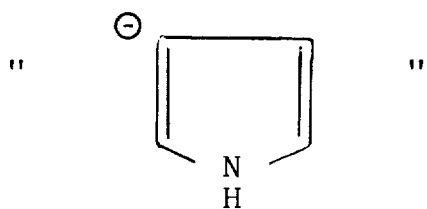

should read:

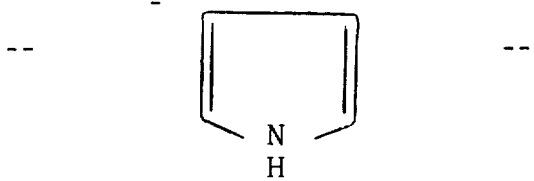

UNITED STATES PATENT AND TRADEMARK OFFICE
CERTIFICATE OF CORRECTION

PATENT NO. : 4,064,138
DATED : December 20, 1977
INVENTOR(S) : Albert L. Saari & Ray H. Anderson It is certified that error appears in the above-identified patent and that said Letters Patent are hereby corrected as shown below:

In column 12, line 36, delete: " D - is $HPO_3F$ - "
    and insert: -- $D^\ominus$ is $HPO_3F^\ominus$ --

In column 12, line 44, delete " $R^+$ " and insert -- $R^\oplus$ --.

In column 12, lines 56-59 approximately, the formula that reads:

" 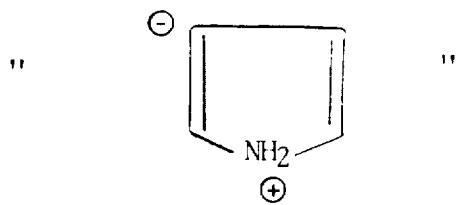 "

should read:

-- 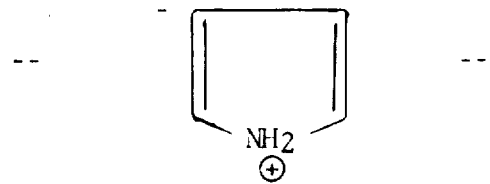 --

UNITED STATES PATENT AND TRADEMARK OFFICE
CERTIFICATE OF CORRECTION

PATENT NO. : 4,064,138
DATED : December 20, 1977
INVENTOR(S) : Albert L. Saari & Ray H. Anderson It is certified that error appears in the above-identified patent and that said Letters Patent are hereby corrected as shown below:

In column 12, line 63, delete: "E - is $HPO_3F$ -."

and insert: -- $E^{\ominus}$ is $HPO_3F^{\ominus}$. --

Signed and Sealed this

Seventeenth Day of October 1978

[SEAL]

Attest:

RUTH C. MASON
Attesting Officer

DONALD W. BANNER
Commissioner of Patents and Trademarks